US007754716B2

(12) United States Patent
Dugan

(10) Patent No.: US 7,754,716 B2
(45) Date of Patent: Jul. 13, 2010

(54) COMBINATION COMPRISING A VASCULOSTATIC COMPOUND AND AN ALKYLATING AGENT FOR THE TREATMENT OF A TUMOR

(75) Inventor: Margaret Han Dugan, Woodside, NY (US)

(73) Assignee: Novartis AG, Basel (CH)

(*) Notice: Subject to any disclaimer, the term of this patent is extended or adjusted under 35 U.S.C. 154(b) by 1260 days.

(21) Appl. No.: 10/518,989

(22) PCT Filed: Jun. 27, 2003

(86) PCT No.: PCT/EP03/06848

§ 371 (c)(1),
(2), (4) Date: Jul. 21, 2005

(87) PCT Pub. No.: WO2004/002485

PCT Pub. Date: Jan. 8, 2004

(65) Prior Publication Data

US 2006/0211674 A1    Sep. 21, 2006

Related U.S. Application Data

(60) Provisional application No. 60/392,589, filed on Jun. 28, 2002.

(51) Int. Cl.
*A61K 31/502* (2006.01)
*C07D 401/06* (2006.01)
*C07D 487/04* (2006.01)
*A61K 31/33* (2006.01)

(52) U.S. Cl. .................... 514/248; 544/237; 544/179; 514/183

(58) Field of Classification Search ................ 514/248, 514/183; 544/237, 179
See application file for complete search history.

(56) References Cited

U.S. PATENT DOCUMENTS 5,939,098 A * 8/1999 Reidenberg et al. ......... 424/451
6,258,812 B1   7/2001 Bold et al. .............. 514/252.03

FOREIGN PATENT DOCUMENTS

| WO | WO 02/41882  | * | 5/2002  |
| WO | WO 02/076926 |   | 10/2002 |
| WO | WO 02/090346 |   | 11/2002 |
| WO | WO 03/031440 |   | 4/2003  |

OTHER PUBLICATIONS

Bocci et al., "Antitumor Activity of SU5416 in Association with Gemcitabine In Vitro and in Mice Bearing MIA PaCa-2 Human Pancreas Adenocarcinoma", *Pancreas*, vol. 21, No. 4, p. 432 (2000).
Browder et al., "Antiangiogenic Scheduling of Chemotherapy Improves Efficacy against Experimental Drug-resistant Cancer", *Cancer Res*, vol. 60, No. 7, pp. 1878-1886 (2001).
Chan et al., "Expression of Vascular Endothelial Growth Factor and Its Receptors in the Anaplastic Progression of Astrocytoma, Oligodendroglioma, and Ependymoma", *Am J Surg Pathol*, vol. 22, No. 7, pp. 816-826 (1998).
Cheng et al., "Suppression of Glioblastoma Angiogenicity and Tumorigenicity by Inhibition of Endogenous Expression of Vascular Endothelial Growth Factor", *Proc Natl Acad Sci USA*, vol. 93, No. 16, pp. 8502-8507 (1996).
Im et al., "Antiangiogenesis Treatment for Gliomas: Transfer of Antisense-Vascular Endothelial Growth Factor Inhibits Tumor Growth in Vivo", *Cancer Res*, vol. 59, No. 4, pp. 895-900 (1999).
Kato et al., "Enhanced Suppression of Tumor Growth by Combination of Angiogenesis Inhibitor O-(chloroacetyl-carbamoyl)fumagillol (TNP-470) and Cytotoxic Agents in Mice", *Cancer Res*, vol. 54, No. 19, pp. 5143-5147 (1994).
Kim et al., "Inhibition of Vascular Endothelial Growth Factor-induced Angiogenesis Suppresses Tumor Growth In Vivo", *Nature*, vol. 362, No. 6423, pp. 841-844 (1993).
Lin et al., "The Vascular Endothelial Growth Factor Receptor Tyrosine Kinase Inhibitor PTK787/ZK222584 Inhibits Growth and Migration of Multiple Myeloma Cells in the Bone Marrow Microenvironment", *Cancer Res*, vol. 62, No. 17, pp. 5019-5026 (2002).
Ma et al., "Pharmacokdynamic-mediated Reduction of Temozolomide Tumor Concentrations by the Angiogenesis Inhibitor TNP-470", *Cancer Res*, vol. 61, No. 14, pp. 5491-5498 (2001).
Mehta et al., "Radiation Therapy Oncology Group. Research Plan 2002-2006. Brain Tumor Committee", *Int J Radiat Oncol Biol Phys*, vol. 51, No. 3, Suppl. 2, pp. 11-18 (2001).
Millauer et al., "Glioblastoma Growth Inhibited In Vivo by a Dominant-negative Flk-1 Mutant", *Nature*, vol. 367, No. 6463, pp. 576-579 (1994).
Newton, "Novel Chemotherapeutic Agents for the Treatment of Brain Cancer", *Expert Opin Investig Drugs*, vol. 9, No. 12, pp. 2815-2829 (2000).
Oehring et al., "Vascular Endothelial Growth Factor (VEGF) in Astrocytic Gliomas—A Prognostic Factor?", *J Neuro-Oncol*, vol. 45, pp. 117-125 (1999).
Plate et al., "Vascular Endothelial Growth Factor is a Potential Tumour Angiogenesis FActor in Human Gliomas In Vivo", *Nature*, vol. 359, No. , pp. 845-848 (1992).
Rosen, "Angiogenesis Inhibition in Solid Tumors", *Cancer J*, vol. 7, Suppl. 3, pp. S120-S128 (2001).
Takano et al., "Concentration of Vascular Endothelial Growth Factor in the Serum and Tumor Tissue of Brian Tumor Patients", *Cancer Res*, vol. 56, No. 9, pp. 2185-2190 (1996).

(Continued)

*Primary Examiner*—Charanjit S Aulakh
(74) *Attorney, Agent, or Firm*—George R. Dohmann

(57) ABSTRACT

The invention relates to a pharmaceutical combination which comprises (a) a vasculostatic compound, (b) an alkylating agent and (c) optionally at least one pharmaceutically acceptable carrier for simultaneous, separate or sequential use for the treatment of a tumor disease; a pharmaceutical composition comprising such a combination; the use of such a combination for the preparation of a medicament for the treatment of a tumor disease; a commercial package or product comprising such a combination as a combined preparation for simultaneous, separate or sequential use; and to a method of treatment of a warm-blooded animal, especially a human.

5 Claims, No Drawings

OTHER PUBLICATIONS

Teicher et al., "Comparison of Several Antiangiogenic Regimens Alone and With Cytotoxic Therapies in the Lewis Lung Carcinoma", *Cancer Chemther Pharmacol*, vol. 38, No. 2, pp. 169-177 (1996).

Weindel, Moringlane, Marme and Weich, "Detection and Quantification of Vascular Endothelial Growth Factor/Vascular Permeability Factor in Brain Tumor Tissue and Cyst Fluid: The Key to Angiogenesis?", *Neurosurgery*, vol. 35, No. 3, pp. 439-449 (1994).

* cited by examiner

COMBINATION COMPRISING A VASCULOSTATIC COMPOUND AND AN ALKYLATING AGENT FOR THE TREATMENT OF A TUMOR

This application claims benefit of U.S. Provisional Application 60/392,589, filed Jun. 28, 2002.

The invention relates to a pharmaceutical combination which comprises (a) a vasculostatic compound, (b) an alkylating agent and (c) optionally at least one pharmaceutically acceptable carrier for simultaneous, separate or sequential use for the treatment of a tumor disease; a pharmaceutical composition comprising such a combination; the use of such a combination for the preparation of a medicament for the treatment of a tumor disease; a commercial package or product comprising such a combination as a combined preparation for simultaneous, separate or sequential use; and to a method of treatment of a warm-blooded animal, especially a human.

The use of vasculostatic compounds for the treatment of proliferative diseases is already known in the art. At the centre of the network regulating the growth and differentiation of the vascular system and its components lies the angiogenic factor known as "Vascular Endothelial Growth Factor", along with its cellular receptors (see Breier, G., et al., Trends in Cell Biology 6, 454-6 [1996] and references cited therein). VEGF is a dimeric, disulfide-linked 46-kDa glycoprotein. VEGF receptors are transmembranous receptor tyrosine kinases. They are characterized by an extracellular domain with seven immunoglobulin-like domains and an intracellular tyrosine kinase domain.

Certain diseases are known to be associated with deregulated angiogenesis, especially proliferative diseases, for example so-called solid tumours and liquid tumours (such as leukaemia). A large number of human tumors express high levels of VEGF and its receptors. Direct evidence of the role of VEGF as a tumor angiogenesis factor in vivo has been obtained from studies in which VEGF expression or VEGF activity was inhibited.

Surprisingly, it has now been found that the anti-proliferative effect of a combination, which comprises a vasculostatic compound and an alkylating agent, is greater than the maximum effect that can be achieved with either type of ingredient alone.

Hence, the present invention pertains to a combination, such as a combined preparation or a pharmaceutical composition, which comprises (a) a vasculostatic compound, preferably, a compound decreasing the activity of the vascular endothelial growth factor (VEGF), and (b) an alkylating agent and (c) optionally at least one pharmaceutically acceptable carrier for simultaneous, separate or sequential use for the treatment of a tumor disease, in which the active ingredients (a) and (b) are present in each case in free form or in the form of a pharmaceutically acceptable salt.

The term "a combined preparation" as used herein defines especially a "kit of parts" in the sense that the combination partners (a) and (b) as defined above can be dosed independently or by the use of different fixed combinations with distinguished amounts of the combination partners (a) and (b). The parts of the kit of parts can then, e.g., be administered simultaneously or chronologically staggered, that is at different time points and with equal or different time intervals for any part of the kit of parts. Very preferably, the time intervals are chosen such that the effect on the treated disease in the combined use of the parts is larger than the effect which would be obtained by use of only any one of the combination partners (a) and (b). The ratio of the total amounts of the combination partner (a) to the combination partner (b) to be administered can be varied, e.g., in order to cope with the needs of a patient sub-population to be treated or the needs of a single patient, which different needs can be due to age, sex, body weight, etc. of the patients. Preferably, there is at least one beneficial effect, e.g., a mutual enhancing of the effect of the combination partners (a) and (b), in particular a synergism, e.g. a more than additive effect, additional advantageous effects, less side effects, a combined therapeutical effect in a non-effective dosage of one or both of the combination partners (a) and (b), and very preferably a strong synergism of the combination partners (a) and (b).

The term "treatment" comprises the administration of the combination partners to a warm-blooded animal in need of such treatment with the aim to effect a delay of progression of a disease.

The term "delay of progression" as used herein means that the tumor growth is at least slowed down or hampered by the treatment and that patients exhibit higher survival rates than patients not being treated or being treated with the monotherapy.

The term "tumor disease" means any neoplastic proliferative disorder e.g. solid tumor diseases, liquid tumor diseases.

The term "a solid tumor disease" as used herein means especially breast cancer, ovarian cancer, cancer of the colon and generally the gastro-intestinal tract, lung cancer, e.g., small-cell lung cancer and non-small-cell lung cancer, renal cancer, bladder cancer, prostate cancer, skin cancer like melanoma, head and neck cancer or a tumor disease of the central nervous system, e.g., cervix cancer and, in particular, a brain tumor, more especially astrocytoma, e.g., glioma.

The term "head and neck cancer" refers to any type of tumor diseases occurring in the head as, for example, mouth cancer.

The term "brain tumor" means any type of brain cancer, i.e., arising from any brain cell type.

The term "glioma" means a brain tumor that originates from glial cells, most often from astrocyte, such as glioblastoma multiforme and anaplastic astrocytoma, anaplastic oligodendroglioma and anaplastic oligoastrocytoma.

The term "alkylating agent" as used herein includes, but is not limited to, alkyl sulfonates, aziridines, epoxides, ethylenimines, methylmelamines, nitrogen mustards, nitrosoureas, imidazotetrazinones, dacarbazine, mannomustine, mitobronitol, mitolactol, pipobroman and procarbazine.

The term "alkyl sulfonates" as used herein includes, but is not limited to, busulfan, improsulfan and piposulfan.

The term "aziridines" as used herein includes, but is not limited to, benzodepa, carboquone, meturedepa and uredepa.

The term "ethylenimines and methylmelamines" as used herein includes, but is not limited to, altretamine, triethylenemelamine, triethylenephosphoramide, triethylenethiophosphoramide and trimethylolmelamine.

The term "nitrogen mustards" as used herein includes, but is not limited to, chlorambucil, chlornaphazine, cyclophosphamide, estramustine, ifosfamide, mechlorethamine, mechlorethamine oxide hydrochloride, melphalan, novembichin, phenesterine, prednimustine, trofosfamide and uracil mustard.

The term "nitrosoureas" as used herein includes, but is not limited to, carmustine, chlorozotocin, cytemustine, fotemustine, lomustine (CCNU), nimustine and ranimustne.

The term "imidazotetrazinones" as used herein includes, but is not limited to, temozolomide and mitozolomide.

"Temozolomide" is described in U.S. Pat. No. 5,260,291. The synthesis of temozolomide is well known e.g., Wang et al., J. Org. Chem. 1997, 62, 7288-7294). Temozolomide is commercially available e.g. under the trademark of TEMODAL™, TEMODAR™, or TEMOXOL™ and can be administered, e.g., as described in U.S. Pat. No. 5,942,247 or according to the package insert information. The term "lomustine" means a compound as described and prepared e.g. in Johnson P et al., J. Med. Chem. 1966, 9, 892. Lomustine is commercially available under the trademark BETU-LUSTINE™ and can be administered according to the package insert information.

The term "vasculostatic compounds" as used herein comprises, but is not restricted to, active ingredients which decrease the activity of the VEGF, metalloproteinase inhibitors and other compounds having a vasculostatic effect.

The active ingredient, which decreases the activity of the VEGF, is especially selected from the group consisting of compounds which inhibit the VEGF receptor tyrosine kinase, compounds which inhibit a VEGF receptor and compounds binding to VEGF. The active ingredient, which decreases the activity of the VEGF, is in particular one of those compounds, proteins and monoclonal antibodies, which are generically and specifically disclosed in WO 98/35958 (describing compounds of formula I), WO 00/09495, WO 00/27820, WO 00/59509, WO 98/11223, WO 00/27819, WO 01/55114, WO 01/58899 and EP 0 769 947, which are described by M. Preweft et al in Cancer Research 59 (1999) 5209-5218, by F. Yuan et al in Proc. Natl. Acad. Sci. USA, vol. 93, pp. 14765-14770, December 1996, by Z. Zhu et al in Cancer Res. 58, 1998, 3209-3214, and by J. Mordenti et al in Toxicologic Pathology, Vol. 27, no. 1, pp 14-21, 1999, those which are generically and specifically disclosed in WO 00137502 and WO 94/10202; and those which are described by M. S. O'Reilly et al, Cell 79, 1994, 315-328 (Angiostatin™) and by M. S. O'Reilly et al, Cell 88, 1997, 277-285 (Endostatin™), in each case in particular in the compound claims, the pharmaceutical preparations and the final products of the working examples, the subject-matter of which is hereby incorporated into the present application by reference to this publications. Comprised are likewise the corresponding stereoisomers as well as the corresponding crystal modifications, e.g. solvates and polymorphs, which are disclosed therein. The compounds used as active ingredients in the combinations disclosed herein can be prepared and administered as described in the cited documents, respectively.

"Metalloproteinase inhibitors" as defined herein are, e.g., Marimastat (BB-2516), Prinomastat (AG3340), Bay 12-9566, BMS-275291, MM1270B and Metastat (NSC 683551).

The term "other compounds having a vasculostatic effect" as defined herein relates in particular to the compounds EMD-121974, doxorubicin, paclitaxel, IM-862, Thalidomide®, Linomide®, PKC412, AGM-1470, Suramin and Pentosan polysulfate.

In particular, the present invention pertains to a combination wherein the vasculostatic compound is a compound of formula I

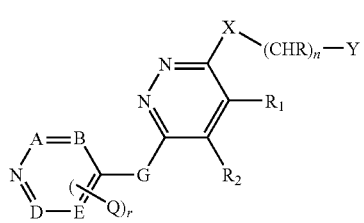

(I)

wherein r is 0 to 2, n is 0 to 2, m is 0 to 4,
$R_1$ and $R_2$ (i) are lower alkyl or
(ii) together form a bridge in subformula I*

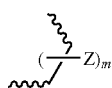

(I*)

the binding being achieved via the two terminal carbon atoms, or
(iii) together form a bridge in subformula I**

(I**)

wherein one or two of the ring members $T_1$, $T_2$, $T_3$ and $T_4$ are nitrogen, and the others are in each case CH, and the binding is achieved via $T_1$ and $T_4$;

A, B, D, and E are, independently of one another, N or CH, with the stipulation that not more than 2 of these radicals are N;

G is lower alkylene, lower alkylene substituted by acyloxy or hydroxy, —CH$_2$—O—, —CH$_2$S—, —CH$_2$—NH—, oxa (—O—), thia (—S—), or imino (—NH—);

Q is lower alkyl;

R is H or lower alkyl;

X is imino, oxa, or thia;

Y is unsubstituted or substituted aryl, pyridyl, or unsubstituted or substituted cycloalkyl; and Z is amino, mono- or disubstituted amino, halogen, alkyl, substituted alkyl, hydroxy, etherified or esterified hydroxy, nitro, cyano, carboxy, esterified carboxy, alkanoyl, carbamoyl, N-mono- or N,N-disubstituted carbamoyl, amidino, guanidino, mercapto, sulfo, phenylthio, phenyl-lower alkylthio, alkylphenylthio, phenylsulfonyl, phenyl-lower alkylsulfinyl or alkylphenylsulfinyl, substituents Z being the same or different from one another if more than 1 radical Z is present;

and wherein the bonds characterized, if present, by a wavy line are either single or double bonds; or an N-oxide of the defined compound, wherein 1 or more N atoms carry an oxygen atom, or the salt of such compound having at least one salt-forming group.

The term "PTK787" as used herein means a compound of formula I wherein r, n and m are each 0, $R_1$ and $R_2$ together form a bridge of subformula I*, A, B, D and E are each CH, G is methylene, X is imino, Y is 4-chlorophenyl, and the bonds characterized by a wavy line are double bonds.

The compounds used as combination partners (a) and (b) disclosed herein can be prepared and administered as described in the cited documents, respectively. The combination partners (a) or (b) and their salts may also be used in the form of a hydrate or include other solvents used for crystallization.

Furthermore, the structure of the active agents mentioned herein by name may be taken from the actual edition of the standard compendium "The Merck Index" or from databases, e.g. Patents International (e.g. IMS World Publications). The corresponding content thereof is hereby incorporated by reference. Any person skilled in the art is fully enabled, based on these references, to manufacture and test the pharmaceutical indications and properties in standard test models, both in vitro and in vivo.

A combination which comprises (a) a vasculostatic compound and (b) an alkylating agent, in which the active ingredients are present in each case in free form or in the form of a pharmaceutically acceptable salt, and optionally at least one pharmaceutically acceptable carrier will be referred to hereinafter as a COMBINATION OF THE INVENTION.

The nature of proliferative diseases like solid tumor diseases is multifactorial. Under certain circumstances, drugs with different mechanisms of action may be combined. However, just considering any combination of drugs having different mode of action does not necessarily lead to combinations with advantageous effects.

All the more surprising is the experimental finding that in vivo the administration of a COMBINATION OF THE INVENTION compared to a monotherapy applying only one of the pharmaceutically active ingredients used in the COMBINATION OF THE INVENTION results not only in a more beneficial, especially synergistic, e.g. anti-proliferative effect, e.g. with regard to the delay of progression of a proliferative disease or with regard to a change in tumor volume, but also in further surprising beneficial effects, e.g. less side-effects and a decreased mortality and morbidity. Furthermore, depending on the particular tumor type a decrease of the tumor volume can be obtained when using a COMBINATION OF THE INVENTION in cases in which by monotherapy no decrease of the tumor volume can be achieved. The COMBINATIONS OF THE INVENTION are also suitable to prevent the metastatic spread of tumors and the growth or development of micrometastases. The COMBINATIONS OF THE INVENTION are in particular suitable for the treatment of patients with advanced cancer who have failed standard systemic therapy. This includes patients having tumor types showing resistance to monotherapy or showing resistance to combinations different from those disclosed herein.

A further benefit is that lower doses of the active ingredients of the COMBINATION OF THE INVENTION can be used, for example, that the dosages need not only often be smaller, but are also applied less frequently, or can be used in order to diminish the incidence of side-effects observed with one of the combination partners alone. This is in accordance with the desires and requirements of the patients to be treated.

It can be shown by established test models that a COMBINATION OF THE INVENTION results in the beneficial effects described herein before. The person skilled in the pertinent art is fully enabled to select a relevant test model to prove such beneficial effects. The pharmacological activity of a COMBINATION OF THE INVENTION may, for example, be demonstrated in a clinical study or in a test procedure as essentially described hereinafter.

Suitable clinical studies are, for example, randomized, double-blind, placebo-controlled, parallel studies in patients with recurrent glioblastoma, but also dose escalation studies. Placebo-controlled studies are, in particular, suitable to compare the effects of a monotherapy using the active ingredients and a therapy using a COMBINATION OF THE INVENTION, and to prove in particular the synergism of the active ingredients of the COMBINATIONS OF THE INVENTION. The primary endpoints in such studies can be the effect on analgesic use, performance status, Quality of Life scores, time to progression of the disease, morbidity, mortality or an increase in the number of stable diseases compared to monotherapy. Tumor assessment in the form of dynamic contrast-enhanced MRI is also a suitable approach to determine the effect of the COMBINATION OF THE INVENTION. In a suitable study design, patients are receiving, for example, temozolomide in a dosage of 50 to 250 mg/m$^2$ daily, for example, 200 mg/m$^2$ daily, for 5 consecutive days every 28 days or placebo in addition to a continuous daily dose of 500 to 2000 mg of a compound of formula I, e.g., 500, 1000, 1500 or 2000 mg of PTK787 or placebo.

It is one objective of this invention to provide a pharmaceutical composition comprising a quantity, which is jointly therapeutically effective against a proliferative disease comprising the COMBINATION OF THE INVENTION. In this composition, the combination partners (a) and (b) can be administered together, one after the other or separately in one combined unit dosage form or in two separate unit dosage forms. The unit dosage form may also be a fixed combination.

The pharmaceutical compositions according to the invention can be prepared in a manner known per se and are those suitable for enteral, such as oral or rectal, and parenteral administration to mammals (warm-blooded animals), including man, comprising a therapeutically effective amount of at least one pharmacologically active combination partner alone or in combination with one or more pharmaceutically acceptable carries, especially suitable for enteral or parenteral application.

The novel pharmaceutical composition contain, for example, from about 10% to about 100%, preferably from about 20% to about 60%, of the active ingredients. Pharmaceutical preparations for the combination therapy for enteral or parenteral administration are, for example, those in unit dosage forms, such as sugar-coated tablets, tablets, capsules or suppositories, and furthermore ampoules. If not indicated otherwise, these are prepared in a manner known per se, for example by means of conventional mixing, granulating, sugar-coating, dissolving or lyophilizing processes. It will be appreciated that the unit content of a combination partner contained in an individual dose of each dosage form need not in itself constitute an effective amount since the necessary effective amount can be reached by administration of a plurality of dosage units.

In particular, a therapeutically effective amount of each of the combination partners of the COMBINATION OF THE INVENTION may be administered simultaneously or sequentially and in any order, and the components may be administered separately or as a fixed combination. For example, the method of treatment of a tumor disease according to the invention may comprise (i) administration of the first combination partner in free or pharmaceutically acceptable salt form and (ii) administration of the second combination partner in free or pharmaceutically acceptable salt form, simultaneously or sequentially in any order, in jointly therapeutically effective amounts, preferably in synergistically effective amounts, e.g. in daily dosages corresponding to the amounts described herein. The individual combination partners of the COMBINATION OF THE INVENTION can be administered separately at different times during the course of therapy or concurrently in divided or single combination forms. Furthermore, the term administering also encompasses the use of a pro-drug of a combination partner that convert in vivo to the combination partner as such. The instant invention is therefore to be understood as embracing all such regimes of simultaneous or alternating treatment and the term "administering" is to be interpreted accordingly.

The effective dosage of each of the combination partners employed in the COMBINATION OF THE INVENTION may vary depending on the particular compound or pharmaceutical composition employed, the mode of administration, the condition being treated, the severity of the condition being treated. Thus, the dosage regimen the COMBINATION OF THE INVENTION is selected in accordance with a variety of factors including the route of administration and the renal and hepatic function of the patient. A physician, clinician or veterinarian of ordinary skill can readily determine and prescribe the effective amount of the single active ingredients required to prevent, counter or arrest the progress of the condition. Optimal precision in achieving concentration of the active ingredients within the range that yields efficacy without toxicity requires a regimen based on the kinetics of the active ingredients' availability to target sites. This involves a consideration of the distribution, equilibrium, and elimination of the active ingredients.

The COMBINATIONS OF THE INVENTION inhibit the growth of tumors. In one preferred embodiment of the invention, the disease to be treated with a COMBINATION OF THE INVENTION is a solid tumor disease, preferably, a brain tumor and, more preferably, glioblastoma, in particular recurrent glioblastoma.

According to the present the invention, preferred combination partners are (a) temozolomide or lomustine and (b) a compound of formula I.

A preferred compound of formula I is PTK787. More preferably, PTK787 is employed in the form of its succinate salt.

When the combination partners, which are employed in the COMBINATION OF THE INVENTION, are applied in the form as marketed as single drugs, their dosage and mode of administration can be in accordance with the information provided on the package insert of the respective marketed drug, if not mentioned herein otherwise.

The dosage of a compound of formula I, especially PTK787, is preferably in the range of about 250 to 2000, more preferably about 500 to 1500, and most preferably 750 to 1250, e.g. 1000 mg/day, especially, if the warm-blooded animal is an adult human.

Temozolomide is preferably administered daily at a dose of 50 to 300 mg/m$^2$/ day, most preferably 200 mg/m$^2$/day in cycles of 5 consecutive days per 28 day cycle. For patients who had prior chemotherapy, treatment is generally started at 150 mg/m$^2$/day.

Lomustine is preferably administered at a single dose of 60 to 180 mg/m$^2$ once every six weeks preferably at a dose of 130 mg/m$^2$.

The COMBINATION OF THE INVENTION can be a combined preparation or a pharmaceutical composition.

The present invention relates to a method of treating a warm-blooded animal having a tumor disease comprising administering to the animal a COMBINATION OF THE INVENTION in a quantity, which is jointly therapeutically effective against a tumor disease and in which the combination partners can also be present in the form of their pharmaceutically acceptable salts. Furthermore, the treatment can comprise surgery or radiotherapy.

Moreover, the present invention also provides a method of inhibiting the formation of metastases in a warm-blooded animal having a tumor disease, in particular a solid tumor disease, which comprises administering to the patient a pharmaceutically effective amount of a COMBINATION OF THE INVENTION in a quantity which is jointly therapeutically effective against said tumor disease and in which the compounds can also be present in the form of their pharmaceutically acceptable salts.

Furthermore, the present invention pertains to the use of a COMBINATION OF THE INVENTION for the treatment of a tumor disease and for the preparation of a medicament for the treatment of a tumor disease.

Additionally, the present invention pertains to the use of an alkylating agent as described herein above, preferably temozolomide or lomustine, in combination with a vasculostatic compound for the preparation of a medicament for the treatment of a tumor disease.

Moreover, the present invention provides a commercial package comprising as active ingredients COMBINATION OF THE INVENTION, together with instructions for simultaneous, separate or sequential use thereof in the treatment of a tumor disease.

EXAMPLE 1

In a patient with histologically confirmed recurrent glioblastoma receiving temozolomide in a dosage of 50 mg/m$^2$ daily for 5 consecutive days every 28 days in addition to a continuous daily dose of 1000 mg of PTK787 a stable disease is observed during the third cycle of the treatment.

What is claimed is:

1. A combination which comprises
   (a) PTK787 or a pharmaceutically acceptable salt thereof and (b) temozolomide,
   in which the active ingredients (a) and (b) are present in each case in free form or in the form of a pharmaceutically acceptable salt for simultaneous, separate or sequential use.

2. A method of treating a patient having a tumor disease which comprises administering to the patient a combination according to claim 1 in a quantity which is jointly therapeutically effective against said tumor disease and in which the compounds can also be present in the form of their pharmaceutically acceptable salts, wherein the tumor disease is glioblastoma.

3. A method of inhibiting the formation of metastases in a patient having a tumor disease which comprises administering to the patient a pharmaceutically effective amount of a combination according to claim 1 in a quantity which is jointly therapeutically effective against said tumor disease and in which the compounds can also be present in the form of their pharmaceutically acceptable salts wherein the tumor disease is glioblastoma.

4. A method according to claim 3 wherein PTK787 is administered in a daily dose between 250 and 2000 mg.

5. A pharmaceutical composition comprising a combination according to claim 1 and at least one pharmaceutically acceptable carrier.

* * * * *